(12) United States Patent
Chen et al.

(10) Patent No.: US 11,863,133 B2
(45) Date of Patent: *Jan. 2, 2024

(54) TRANS-IMPEDANCE AMPLIFIER FOR ULTRASOUND DEVICE AND RELATED APPARATUS AND METHODS

(71) Applicant: BFLY OPERATIONS, INC., Burlington, MA (US)

(72) Inventors: Kailiang Chen, Branford, CT (US); Keith G. Fife, Palo Alto, CA (US); Nevada J. Sanchez, Guilford, CT (US); Andrew J. Casper, Clinton, CT (US); Tyler S. Ralston, Clinton, CT (US)

(73) Assignee: BFLY OPERATIONS, INC., Burlington, MA (US)

( * ) Notice: Subject to any disclaimer, the term of this patent is extended or adjusted under 35 U.S.C. 154(b) by 289 days.

This patent is subject to a terminal disclaimer.

(21) Appl. No.: 17/331,538

(22) Filed: May 26, 2021

(65) Prior Publication Data

US 2021/0384872 A1 Dec. 9, 2021

Related U.S. Application Data

(63) Continuation of application No. 16/178,117, filed on Nov. 1, 2018, now Pat. No. 11,128,267, which is a
(Continued)

(51) Int. Cl.
*H03F 3/16* (2006.01)
*H03F 1/08* (2006.01)
(Continued)

(52) U.S. Cl.
CPC ............ *H03F 3/16* (2013.01); *A61B 5/6801* (2013.01); *A61B 8/4444* (2013.01);
(Continued)

(58) Field of Classification Search
None
See application file for complete search history.

(56) References Cited

U.S. PATENT DOCUMENTS 3,367,173 A 2/1968 Uphoff
3,787,803 A 1/1974 Beebe
(Continued)

FOREIGN PATENT DOCUMENTS

CN 1832338 A 9/2006
CN 103607130 A 2/2014
(Continued)

OTHER PUBLICATIONS

Indian Examination Report dated Jan. 31, 2022 issued in corresponding Indian Appln. No. 201817019924.
(Continued)

*Primary Examiner* — Hovhannes Baghdasaryan
(74) *Attorney, Agent, or Firm* — Carter, DeLuca & Farrell LLP (57) ABSTRACT

A variable current trans-impedance amplifier (TIA) for an ultrasound device is described. The TIA may be coupled to an ultrasonic transducer to amplify an output signal of the ultrasonic transducer representing an ultrasound signal received by the ultrasonic transducer. During acquisition of the ultrasound signal by the ultrasonic transducer, one or more current sources in the TIA may be varied.

20 Claims, 6 Drawing Sheets

Related U.S. Application Data continuation of application No. 14/957,395, filed on Dec. 2, 2015, now Pat. No. 10,187,020.

(51) Int. Cl.
  *H03F 3/45*     (2006.01)
  *G01S 7/52*     (2006.01)
  *A61B 5/00*     (2006.01)
  *A61B 8/00*     (2006.01)
  *A61B 8/08*     (2006.01)

(52) U.S. Cl.
  CPC .......... *G01S 7/52025* (2013.01); *H03F 1/086* (2013.01); *H03F 3/45183* (2013.01); *A61B 8/5207* (2013.01); *H03F 2200/408* (2013.01); *H03F 2200/555* (2013.01); *H03F 2203/45471* (2013.01); *H03F 2203/45504* (2013.01); *H03F 2203/45631* (2013.01); *H03F 2203/45634* (2013.01); *H03F 2203/45646* (2013.01); *H03F 2203/45648* (2013.01); *H03F 2203/45674* (2013.01); *H03F 2203/45686* (2013.01); *H03F 2203/45692* (2013.01); *H03F 2203/45726* (2013.01)

(56) References Cited

U.S. PATENT DOCUMENTS

| | | | |
|---|---|---|---|
| 4,098,130 A | 7/1978 | Coffey et al. | |
| 4,504,747 A | 3/1985 | Smith et al. | |
| 4,512,350 A | 4/1985 | Cimilluca | |
| 4,783,819 A | 11/1988 | De Koning et al. | |
| 4,819,071 A | 4/1989 | Nakamura | |
| 5,057,719 A | 10/1991 | Niedra | |
| 3,274,821 A | 9/1996 | Weighart | |
| 5,622,177 A | 4/1997 | Breimesser et al. | |
| 5,844,445 A | 12/1998 | Takeyari | |
| 5,942,940 A | 8/1999 | Dreps et al. | |
| 6,404,281 B1 | 6/2002 | Kobayashi | |
| 7,176,720 B1 | 2/2007 | Prather et al. | |
| 7,256,654 B2 | 8/2007 | White et al. | |
| 7,313,053 B2 | 12/2007 | Wodnicki | |
| 7,449,958 B1 | 11/2008 | Voo | |
| 7,605,660 B1 | 10/2009 | Kobayashi | |
| 8,089,309 B2 | 1/2012 | Jansen et al. | |
| 8,662,395 B2 | 3/2014 | Melandso et al. | |
| 8,766,721 B1 | 7/2014 | Dusad | |
| 8,852,103 B2 | 10/2014 | Rothberg et al. | |
| 9,112,521 B2 | 8/2015 | Dedic et al. | |
| 9,229,097 B2 | 1/2016 | Rothberg et al. | |
| 9,473,136 B1 | 10/2016 | Chen et al. | |
| 9,492,144 B1 | 11/2016 | Chen et al. | |
| 9,705,518 B2 | 7/2017 | Chen et al. | |
| 9,933,516 B2 | 4/2018 | Chen et al. | |
| 9,958,537 B2 | 5/2018 | Chen et al. | |
| 10,014,871 B2 | 7/2018 | Chen et al. | |
| 10,082,488 B2 | 9/2018 | Chen et al. | |
| 10,175,347 B2 | 1/2019 | Chen et al. | |
| 10,187,020 B2 | 1/2019 | Chen et al. | |
| 10,277,236 B2 | 4/2019 | Chen et al. | |
| 10,624,613 B2 | 4/2020 | Ralston | |
| 10,707,886 B2 | 7/2020 | Chen et al. | |
| 11,215,703 B2 | 1/2022 | Chen et al. | |
| 11,275,161 B2 | 3/2022 | Chen et al. | |
| 2005/0203392 A1 | 9/2005 | Petersen et al. | |
| 2005/0206412 A1 | 9/2005 | Moraveji | |
| 2007/0001764 A1 | 1/2007 | Huang et al. | |
| 2007/0242567 A1 | 10/2007 | Daft et al. | |
| 2007/0287923 A1 | 12/2007 | Adkins et al. | |
| 2008/0225639 A1 | 9/2008 | Hongou | |
| 2009/0140810 A1 | 6/2009 | Kim et al. | |
| 2009/0250729 A1 | 10/2009 | Lemmerhirt et al. | |
| 2009/0289716 A1 | 11/2009 | Jaeger et al. | |
| 2010/0026343 A1 | 2/2010 | Yang et al. | |
| 2010/0152587 A1 | 6/2010 | Haider et al. | |
| 2010/0237807 A1 | 9/2010 | Lemmerhirt | |
| 2010/0317972 A1 | 12/2010 | Baumgartner et al. | |
| 2011/0055447 A1 | 3/2011 | Costa | |
| 2012/0262221 A1 | 10/2012 | Bottarel et al. | |
| 2013/0064043 A1 | 3/2013 | Degertekin et al. | |
| 2013/0106485 A1 | 5/2013 | Mukhopadhyay et al. | |
| 2013/0187697 A1 | 7/2013 | Choy et al. | |
| 2013/0314154 A1 | 11/2013 | Yoshikawa | |
| 2014/0078866 A1 | 3/2014 | Kanamori et al. | |
| 2014/0288428 A1 | 9/2014 | Rothberg et al. | |
| 2015/0032002 A1 | 1/2015 | Rothberg et al. | |
| 2015/0297193 A1 | 10/2015 | Rothberg et al. | |
| 2017/0160239 A1 | 6/2017 | Chen et al. | |
| 2017/0160387 A1 | 6/2017 | Chen et al. | |
| 2017/0160388 A1 | 6/2017 | Chen et al. | |
| 2017/0163225 A1 | 6/2017 | Chen et al. | |
| 2017/0163276 A1 | 6/2017 | Chen et al. | |
| 2017/0202541 A1 | 7/2017 | Ralston | |
| 2017/0264307 A1 | 9/2017 | Chen et al. | |
| 2017/0307739 A1 | 10/2017 | Chen et al. | |
| 2018/0210073 A1 | 7/2018 | Chen et al. | |
| 2018/0262200 A1 | 9/2018 | Chen et al. | |
| 2018/0364200 A1 | 12/2018 | Chen et al. | |
| 2019/0086525 A1 | 3/2019 | Chen et al. | |
| 2019/0140603 A1 | 5/2019 | Chen et al. | |
| 2019/0253061 A1 | 8/2019 | Chen et al. | |
| 2019/0336111 A1 | 11/2019 | Chen et al. | |
| 2020/0150252 A1 | 5/2020 | Chen et al. | |

FOREIGN PATENT DOCUMENTS

| | | |
|---|---|---|
| EP | 1 932 479 A1 | 6/2008 |
| FR | 2 726 408 A1 | 5/1996 |
| JP | 04-062494 | 2/1992 |
| JP | H06-085585 A | 3/1994 |
| JP | H11-261764 A | 9/1999 |
| JP | 2002-125969 A | 5/2002 |
| JP | 2006-061695 A | 3/2006 |
| JP | 2008-042521 A | 2/2008 |
| JP | 2010-022761 A | 2/2010 |
| JP | 2010-034855 A | 2/2010 |
| JP | 2010-042146 A | 2/2010 |
| JP | 2010-167167 A | 8/2010 |
| JP | 2010-193329 A | 9/2010 |
| JP | 2012-528685 A | 11/2012 |
| JP | 2013-247536 A | 12/2013 |
| JP | 2014-198234 A | 10/2014 |
| JP | 2014-204195 A | 10/2014 |
| JP | 2015-033123 A | 2/2015 |
| JP | 2015-056890 A | 3/2015 |
| JP | 2015-115883 A | 6/2015 |
| JP | 2006-345481 A | 12/2016 |
| KR | 10-1024849 B1 | 3/2011 |
| TW | 201445554 A | 12/2014 |

OTHER PUBLICATIONS

International Search Report and Written Opinion dated Feb. 7, 2017 for Application No. PCT/US2016-064314.

International Preliminary Report on Patentability dated Jun. 14, 2018 in connection with International Application No. PCT/US2016/064314.

International Search Report and Written Opinion dated Jan. 29, 2020 for Application No. PCT/US2019/060399.

Extended European Search Report dated Jun. 18, 2019 in connection with European Application No. 16871486.3.

Extended European Search Report dated Jul. 18, 2019 in connection with European Application No. 16871492.1.

Extended European Search Report dated Jun. 17, 2019 in connection with European Application No. 16871500.1.

Extended European Search Report dated May 28, 2019 in connection with European Application No. 16871466.5.

Extended European Search Report dated Jun. 4, 2019 in connection with European Application No. 16871463.2.

Taiwanese Office Action dated Jan. 19, 2018 in connection with Taiwanese Application No. 105139662 .

(56) References Cited

OTHER PUBLICATIONS

Agarwal et al., Single-Chip Solution for Ultrasound Imaging Systems: Initial Results. 2007 IEEE Ultrasonics Symposium. Oct. 1, 2007;1563-6.

Chen et al., Ultrasonic Imaging Front-End Design for CMUT: A 3-Level 30Vpp Pulse-Shaping Pulser with Improved Efficiency and a Noise-Optimized Receiver. IEEE Asian Solid-State Circuits Conference. Nov. 12-14, 2012;173-6.

Cheng et al., An Efficient Electrical Addressing Method Using Through-Wafer Vias for Two-Dimensional Ultrasonic Arrays. 2000 IEEE Ultrasonics Symposium. 2000;2:1179-82.

Cheng et al., CMUT-in-CMOS ultrasonic transducer arrays with on-chip electronics. Transducers 2009. IEEE. Jun. 21, 2009;1222-5.

Cheng et al., Electrical Through-Wafer Interconnects with Sub-PicoFarad Parasitic Capacitance. 2001 Microelectromech Syst Conf. Aug. 24, 2001;18-21.

Daft et al., 5F-3 A Matrix Transducer Design with Improved Image Quality and Acquisition Rate. 2007 IEEE Ultrasonics Symposium. Oct. 1, 2007;411-5.

Daft et al., Microfabricated Ultrasonic Transducers Monolithically Integrated with High Voltage Electronics. 2004 IEEE Ultrasonics Symposium. Aug. 23, 2004;1:493-6.

Gurun et al., Front-end CMOS electronics for monolithic integration with CMUT arrays: circuit design and initial experimental results. Proc Ultrason Symp. 2008;390-3.

Khuri-Yakub et al., Miniaturized Ultrasound Imaging Probes Enabled by CMUT Arrays with Integrated Frontend Electronic Circuits. Conf Proc IEEE Eng Med Biol Soc. 2010;1:5987-90. doi: 10.1109/IEMBS.2010.5627580. Epub Dec. 6, 2010. 13 pages.

Kim et al., Design and Test of A Fully Controllable 64x128 2-D CMUT Array Integrated with Reconfigurable Frontend ASICs for Volumetric Ultrasound Imaging. IEEE. International Ultrasonics Symposium Proceedings. Oct. 7-10, 2012;77-80. doi: 10.1109/ULTSYM.2012.0019.

Orozco, Programmable-Gain Transimpedance Amplifiers Maximize Dynamic Range in Spectroscopy Systems. Analog Dialogue. May 2013;47(05):1-5.

Reyes et al., A 2GS/s 6-bit CMOS time-interleaved ADC for analysis of mixed-signal calibration techniques. Analog Integrated Circuits and Signal Processing. Springer New York LLC. Jul. 3, 2015; 85(1):3-16.

Um et al., An Analog-digital-hybrid single-chip RX beamformer with non-uniform sampling for 2D-CMUT ultrasound imaging to achieve wide dynamic range of delay and small chip area. IEEE International Solid State Circuits Conference. IEEE Service Center. Feb. 9, 2014; pp. 427-427.

TRANS-IMPEDANCE AMPLIFIER FOR ULTRASOUND DEVICE AND RELATED APPARATUS AND METHODS

CROSS-REFERENCE TO RELATED APPLICATIONS

This Application is a continuation claiming the benefit under 35 U.S.C. § 120 of U.S. application Ser. No. 16/178,117, filed Nov. 1, 2018 under Attorney Docket No. B1348.70023US01, and entitled "TRANS-IMPEDANCE AMPLIFIER FOR ULTRASOUND DEVICE AND RELATED APPARATUS AND METHODS", which is hereby incorporated herein by reference in its entirety.

U.S. application Ser. No. 16/178,117 is a continuation of U.S. application Ser. No. 14/957,395, filed Dec. 2, 2015 under Attorney Docket No. B1348.70023US00, and entitled "TRANS-IMPEDANCE AMPLIFIER FOR ULTRASOUND DEVICE AND RELATED APPARATUS AND METHODS", which is hereby incorporated herein by reference in its entirety.

BACKGROUND

Field

The present application relates to ultrasound devices having an amplifier for amplifying received ultrasound signals.

Related Art

Ultrasound probes often include one or more ultrasound sensors which sense ultrasound signals and produce corresponding electrical signals. The electrical signals are processed in the analog or digital domain. Sometimes, ultrasound images are generated from the processed electrical signals.

BRIEF SUMMARY

According to an aspect of the present application, an ultrasound apparatus is provided, comprising an ultrasound sensor and a variable current trans-impedance amplifier (TIA). The variable current TIA is coupled to the ultrasound sensor and configured to receive and amplify an output signal from the ultrasound sensor. The variable current TIA has a variable current source.

According to an aspect of the present application, a method is provided, comprising acquiring an ultrasound signal with an ultrasound sensor during an acquisition period and outputting, from the ultrasound sensor, an analog electrical signal representing the ultrasound signal. The method further comprises amplifying the electrical signal with a variable current trans-impedance amplifier (TIA), including varying a current of the variable current TIA during the acquisition period.

According to an aspect of the present application, a method is provided, comprising acquiring an ultrasound signal with an ultrasound sensor during an acquisition period and outputting, from the ultrasound sensor, an analog electrical signal representing the ultrasound signal. The method further comprises amplifying the electrical signal with a variable current trans-impedance amplifier (TIA), including decreasing a noise floor of the variable current TIA during the acquisition period.

BRIEF DESCRIPTION OF DRAWINGS

Various aspects and embodiments of the application will be described with reference to the following figures. It should be appreciated that the figures are not necessarily drawn to scale. Items appearing in multiple figures are indicated by the same reference number in all the figures in which they appear.

DETAILED DESCRIPTION

Aspects of the present application relate to amplification circuitry for an ultrasound device. An ultrasound device may include one or more ultrasonic transducers configured to receive ultrasound signals and produce electrical output signals. Thus, the ultrasonic transducers may be operated as ultrasound sensors. The ultrasound device may include one or more amplifiers for amplifying the electrical output signals. The power consumed by, the noise generated by, and the linear signal amplification quality provided by, the amplifier may depend on an amount of current consumed by the amplifier. In some embodiments, the amplifier has a variable current source. The variable current source is adjusted during acquisition of an ultrasound signal to maintain the noise level of the amplifier below the signal level and to maintain linear amplification, while at the same time reducing the amount of power consumed by the amplifier. In some embodiments, the amplifier is a TIA.

The aspects and embodiments described above, as well as additional aspects and embodiments, are described further below. These aspects and/or embodiments may be used individually, all together, or in any combination of two or more, as the application is not limited in this respect.

Figure 1:
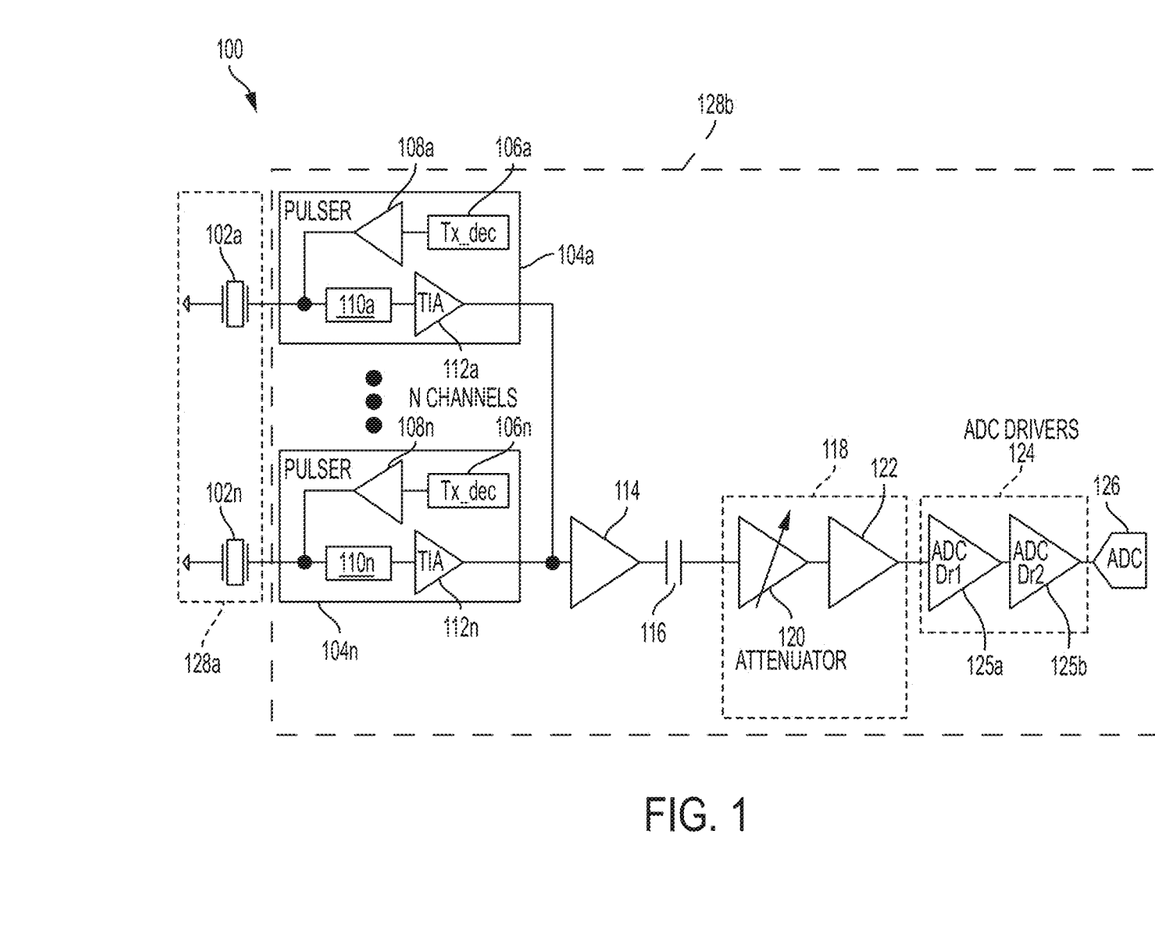
FIG. 1 is a block diagram of an ultrasound device including an amplifier for amplifying an ultrasound signal, according to a non-limiting embodiment of the present application.

FIG. 1 illustrates a circuit for processing received ultrasound signals, according to a non-limiting embodiment of the present application. The circuit 100 includes N ultrasonic transducers 102a . . . 102n, wherein N is an integer. The ultrasonic transducers are sensors in some embodiments, producing electrical signals representing received ultrasound signals. The ultrasonic transducers may also transmit ultrasound signals in some embodiments. The ultrasonic transducers may be capacitive micromachined ultrasonic transducers (CMUTs) in some embodiments. The ultrasonic transducers may be piezoelectric micromachined ultrasonic transducers (PMUTs) in some embodiments. Further alternative types of ultrasonic transducers may be used in other embodiments.

The circuit 100 further comprises N circuitry channels 104a . . . 104n. The circuitry channels may correspond to a respective ultrasonic transducer 102a . . . 102n. For example, there may be eight ultrasonic transducers 102a . . . 102n and eight corresponding circuitry channels 104a . . . 104n. In some embodiments, the number of ultrasonic transducers 102a . . . 102n may be greater than the number of circuitry channels.

The circuitry channels 104a . . . 104n may include transmit circuitry, receive circuitry, or both. The transmit circuitry may include transmit decoders 106a . . . 106n coupled to respective pulsers 108a . . . 108n. The pulsers 108a . . . 108n may control the respective ultrasonic transducers 102a . . . 102n to emit ultrasound signals.

Figure 3A:
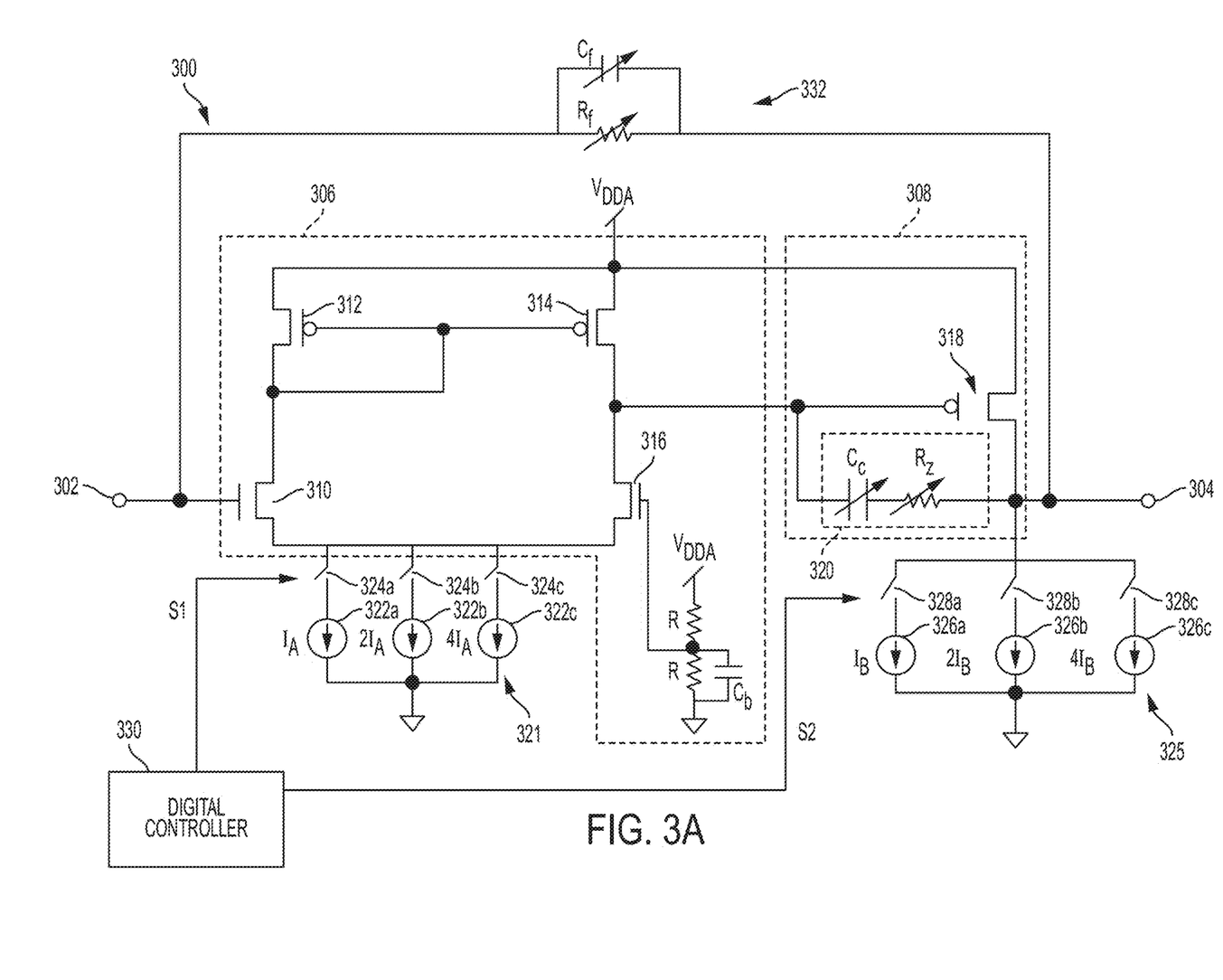
FIG. 3A is a circuit diagram illustrating an implementation of the amplifier of FIG. 2, according to a non-limiting embodiment of the present application.

The receive circuitry of the circuitry channels 104a. . . 104n may receive the electrical signals output from respective ultrasonic transducers 102a . . . 102n. In the illustrated example, each circuitry channel 104a . . . 104n includes a respective receive switch 110a . . . 110n and an amplifier 112a . . . 112n. The receive switches 110a . . . 110n may be controlled to activate/deactivate readout of an electrical signal from a given ultrasonic transducer 102a . . . 102n. More generally, the receive switches 110a . . . 110n may be receive circuits, since alternatives to a switch may be employed to perform the same function. The amplifiers 112a . . . 112n, as well as amplifier 300 of FIG. 3 (described below), may be TIAs in some embodiments. One or more of the amplifiers 112a . . . 112n may be variable current amplifiers. As will be described further below, the current of the amplifiers may be varied during an acquisition period, thus adjusting the power consumption, noise level, and linearity of the amplifiers. The amplifiers 112a . . . 112n may output analog signals.

The circuit 100 further comprises an averaging circuit 114, which is also referred to herein as a summer or a summing amplifier. In some embodiments, the averaging circuit 114 is a buffer or an amplifier. The averaging circuit 114 may receive output signals from one or more of the amplifiers 112a . . . 112n and may provide an averaged output signal. The averaged output signal may be formed in part by adding or subtracting the signals from the various amplifiers 112a . . . 112n. The averaging circuit 114 may include a variable feedback resistance. The value of the variable feedback resistance may be adjusted dynamically based upon the number of amplifiers 112a . . . 112n from which the averaging circuit receives signals. In some embodiments, the variable resistance may include N resistance settings. That is, the variable resistance may have a number of resistance settings corresponding to the number of circuitry channels 104a . . . 104n. Thus, the average output signal may also be formed in part by application of the selected resistance to the combined signal received at the inputs of the averaging circuit 114.

The averaging circuit 114 is coupled to an auto-zero block 116. The auto-zero block 116 is coupled to a programmable gain amplifier 118 which includes an attenuator 120 and a fixed gain amplifier 122. The programmable gain amplifier 118 is coupled to an ADC 126 via ADC drivers 124. In the illustrated example, the ADC drivers 124 include a first ADC driver 125a and a second ADC driver 125b. The ADC 126 digitizes the signal(s) from the averaging circuit 114.

While FIG. 1 illustrates a number of components as part of a circuit of an ultrasound device, it should be appreciated that the various aspects described herein are not limited to the exact components or configuration of components illustrated. For example, aspects of the present application relate to the amplifiers 112a . . . 112n, and the components illustrated downstream of those amplifiers in circuit 100 are optional in some embodiments.

The components of FIG. 1 may be located on a single substrate or on different substrates. For example, as illustrated, the ultrasonic transducers 102a . . . 102n may be on a first substrate 128a and the remaining illustrated components may be on a second substrate 128b. The first and/or second substrates may be semiconductor substrates, such as silicon substrates. In an alternative embodiment, the components of FIG. 1 may be on a single substrate. For example, the ultrasonic transducers 102a . . . 102n and the illustrated circuitry may be monolithically integrated on the same semiconductor die. Such integration may be facilitated by using CMUTs as the ultrasonic transducers.

According to an embodiment, the components of FIG. 1 form part of an ultrasound probe. The ultrasound probe may be handheld. In some embodiments, the components of FIG. 1 form part of an ultrasound patch configured to be worn by a patient.

Figure 2:
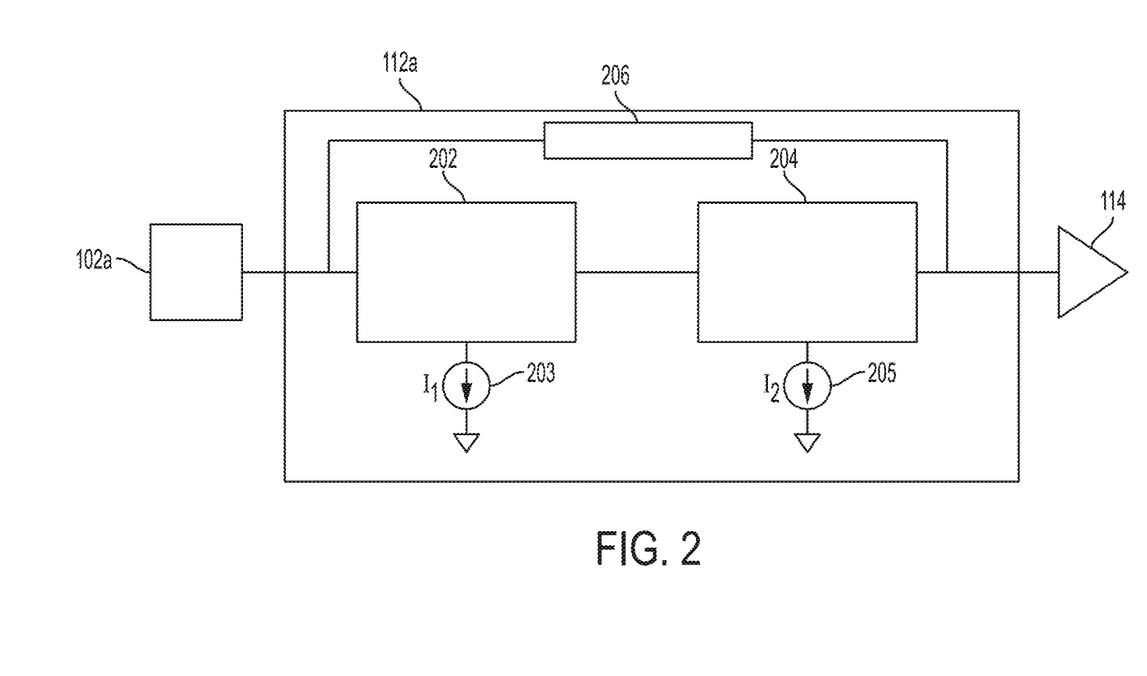
FIG. 2 illustrates the amplifier of FIG. 1 in greater detail, coupled to the ultrasonic transducer and averaging circuit of FIG. 1, according to a non-limiting embodiment of the present application.

FIG. 2 illustrates a non-limiting example of the amplifier 112a of FIG. 1 in greater detail. The same configuration may be used for the other amplifiers 112n of FIG. 1. For context, the ultrasonic transducer 102a and averaging circuit 114 are also illustrated, while for simplicity the receive switch 110a is omitted.

In this non-limiting embodiment, the amplifier 112a is implemented as a two-stage operational amplifier ("op-amp" for short). The first stage 202 is coupled to the ultrasonic transducer 102a. The second stage 204 is coupled between the first stage 202 and the averaging circuit 114. The second stage 204 provides the output signal of the amplifier 112a, in this non-limiting example.

The first stage 202 and second stage 204 each have a variable current source. The variable current source 203 is provided for the first stage 202 and sinks a current I1. The variable current source 205 is provided for the second stage 204 and sinks a current I2. Although the variable current sources 203 and 205 are illustrated as distinct from the respective stages 202 and 204, they may be considered part of the respective stages.

With a two-stage amplifier construction as shown in FIG. 2, the noise and linearity of the amplified signal may be controlled independently. The noise of the amplifier 112a is impacted primarily by the first stage 202. The linearity of the amplifier 112a is impacted primarily by the second stage 204. More generally, the same may be true for a multi-stage amplifier having two or more stages, such that the noise of the amplifier is impacted primarily by the first stage and the linearity of the amplifier is impacted primarily by the last stage. Applicant has appreciated that during acquisition of an ultrasound signal, referred to herein as an acquisition period, the noise and linearity of the amplified signal may vary in importance. When the ultrasound signal is initially received, early in the acquisition period and corresponding to shallow depths when the ultrasound signal is a reflected signal, the associated noise will be relatively low compared to the received signal amplitude, but the linearity of the amplified signal may be of relatively high importance. However, later during the acquisition period, corresponding to greater depths when the ultrasound signal is a reflected signal, the ultrasound signal is likely to become smaller, and thus the noise of the signal is of increased importance. Thus, the amplifier 112a of FIG. 2 is designed to allow for independent and variable control of noise and linearity. The control may be provided via the variable current sources 203 and 205.

Early during an acquisition period, the variable current source 203 may be controlled to sink a relatively small amount of current, while the current source 205 may be controlled to sink a relatively large amount of current. In such a scenario, the second stage 204 may operate to control the linearity of the amplified signal produced by the amplifier 112a, while the first stage 202 may control the noise of the amplified signal 202 to a lesser extent than that to which it is capable. Later in the acquisition period, the current sunk by the variable current source 203 may be increased while the current sunk by the variable current source 205 may be decreased. As the current sunk by the variable current source 203 is increased, the first stage 202 may operate to control the noise of the amplifier 112a to a greater extent. As the current sunk by the variable current source 205 is decreased, the second stage 204 may operate to control the linearity of the amplifier 112a to a lesser extent. Thus, dynamic current biasing of the amplifier 112a, and first stage 202 and second stage 204 more specifically, may be implemented to control the power, noise, and linearity characteristics of the amplifier during an acquisition period.

The dynamic control of current sources 203 and 205 may be achieved using a digital controller, an example being shown in FIG. 3A. The variable current sources 203 and 205 may each include two or more programmable current settings. The greater the number of settings, the greater the control over the current sunk by the current sources 203 and 205.

The amplifier 112a also includes a variable feedback impedance 206. In some embodiments, the variable feedback impedance is a variable RC feedback circuit. An example of the variable RC feedback circuit is illustrated in FIG. 3A and described in connection with that figure. The feedback impedance determines the transimpedance gain of the transimpedance amplifier, such that the input current signal may be converted into an output voltage of varying amplitude.

It should be appreciated from FIG. 2 and the foregoing description that an embodiment of the application provides a multi-stage TIA having two or more independently controllable variable current sources, with a variable feedback impedance. The variable current sources may allow for dynamic current biasing of the TIA, for example during an acquisition period. Thus, the power consumption, noise, and linearity of the amplifier may be adjusted during the acquisition period.

FIG. 3A is a circuit diagram illustrating an implementation of the amplifier 112a of FIG. 2, according to a non-limiting embodiment of the present application. The amplifier 300 has an input 302 and an output 304. The input 302 may be coupled to an ultrasonic transducer or a receive switch, as described previously in connection with FIGS. 1 and 2, and may receive an electrical signal representing an ultrasound signal received by the ultrasonic transducer. The output 304 may provide an amplified output signal of the amplifier 112a, and may be coupled to an averaging circuit or other component to which it is desired to provide the amplified output signal.

The amplifier 300 includes a first stage 306 and a second stage 308, which may be implementations of the first stage 202 and second stage 204 of FIG. 2, respectively. The first stage 306 includes an NMOS transistor 310 having a gate configured to receive the signal at input 302. PMOS transistor 312 and PMOS transistor 314 have their gates coupled, with the drain of PMOS transistor 312 coupled to the drain of NMOS transistor 310. The gate of transistor 312 is coupled to its drain. Transistors 312 and 314 are also configured to receive a power supply voltage VDDA. The first stage 306 further comprises NMOS transistor 316 having a gate configured to receive a bias voltage provided by an RC circuit. The RC circuit includes two resistors, of value R, with a capacitor $C_b$ coupled in parallel with one of the resistors. The other resistor receives the power supply voltage VDDA. The drain of PMOS transistor 314 is coupled to the drain of NMOS transistor 316. An example value for R is 50 kOhm and an example value for $C_b$ is 10 pF, although alternatives for both are possible, such as +/−20% of those values listed, or any value or range of values within such ranges.

The second stage 308 includes a PMOS transistor 318 configured to receive the output of the first stage 306. In particular, the gate of PMOS transistor 318 is coupled to a node between transistors 314 and 316 of the first stage 306. The source of PMOS transistor 318 receives VDDA. A variable impedance circuit 320 is also provided in the second stage 308. The variable impedance circuit 320 includes a variable capacitor $C_C$ in series with a variable resistor $R_Z$, and thus is a variable RC circuit in this embodiment. Variable impedance circuit 320 may provide stable operation of the amplifier 300 when the gain of the amplifier, or the currents of the currents sources, are varied. Thus, the variable impedance circuit may be provided to maintain stable operation of the amplifier 300 for all the current magnitudes sunk by the variable current sources 321 and 325. That is, the values of $C_C$ and $R_Z$ may be adjusted during operation of the amplifier 300 to account for the different current settings programmed by the digital controller 330

A variable current source is provided for each of the stages 306 and 308. The variable current source 321 for the first stage 306 includes three parallel connected current sources 322a, 322b, and 322c. Current source 322a sinks a current $I_A$, current source 322b sinks a current $2I_A$, and current source 322c sinks a current $4I_A$. The current sources 322a-322c are coupled to the first stage 306 by respective switches 324a, 324b, and 324c, which effectively provides 3 bits (8 states) of control of the current. The current $I_A$ may equal 100 microAmps or +/−20% of that value, or any value or range of values within such ranges, as examples.

The variable current source 325 for the second stage 308 includes three parallel connected current sources 326a, 326b, and 326c. Current source 326a sinks a current $I_B$, current source 326b sinks a current $2I_B$, and current source 326c sinks a current $4I_B$. The current sources 326a-326c are coupled to the second stage 308 by respective switches 328a, 328b, and 328c, which effectively provides 3 bits (8 states) of control of the current. The current $I_B$ may equal 50 microAmps or +/−20% of that value, or any value or range of values within such ranges, as examples.

While FIG. 3A illustrates variable current sources each include three parallel-coupled current sources, it should be appreciated that not all aspects of the present application are limited in this manner. That is, variable current sources may be implemented in various manners, including alternative manners to those illustrated. For example, more or fewer than three current sources may be coupled in parallel to create a variable current source. Also, the magnitudes of the current sources may be different than those illustrated in FIG. 3A. Any suitable magnitudes may be provided to allow for operation over a desired range of currents.

A digital controller 330 is provided to control operation of the variable current sources 321 and 325. The digital controller provides control signals to (digitally) program the currents of the variable current sources. In the illustrated example, the digital controller 330 provides one or more switching signals S1 to control operation of the switches 324a-324c, and one or more switching signals S2 to control operation of the switches 328a-328c. In this manner, the amount of current sunk by the variable current sources may be varied independently during operation of the amplifier 300, for example during an acquisition period. According to a non-limiting example, the digital controller 330 decreases the current sunk by variable current source 325 during the acquisition period and increases the current sunk by variable current source 321 during the acquisition period through suitable operation of the switching signals S1 and S2.

The digital controller 330 may be any suitable type of controller. The digital controller may include integrated circuitry. In some embodiments, the digital controller 330 may include or be part of an application specific integrated circuit (ASIC). In some embodiments, the digital controller 330 may not be specific to the amplifier 300. For example, a digital controller may be provided to control more than one component of the circuit of FIG. 1, one of which may be the amplifiers 112a . . . 112n.

The amplifier 300 further includes a variable feedback impedance 332 formed by variable capacitor $C_f$ and variable resistor $R_f$. The capacitor $C_f$ and resistor $R_f$ may be coupled between the output 304 and the input 302, and may be in parallel with each other. The variable feedback impedance 332 may control the gain of the amplifier 300. Thus, the values of $C_f$ and $R_f$ may be adjusted to vary the amplifier's gain.

The variable feedback impedance 332 and the variable impedance circuit 320 may be controlled in any suitable manner. In one embodiment, the digital controller 330 may set the values of the feedback impedances. However, alternatives manners of control may be used.

It should be appreciated that the described groupings of components in connection with FIG. 3A are not limiting. For example, while certain components illustrated in that figure are described as being part of a first stage or a second stage, the identification of the first and second stages is not limiting. The first and second stages may include more, fewer, or different components than those illustrated.

Figure 3B:
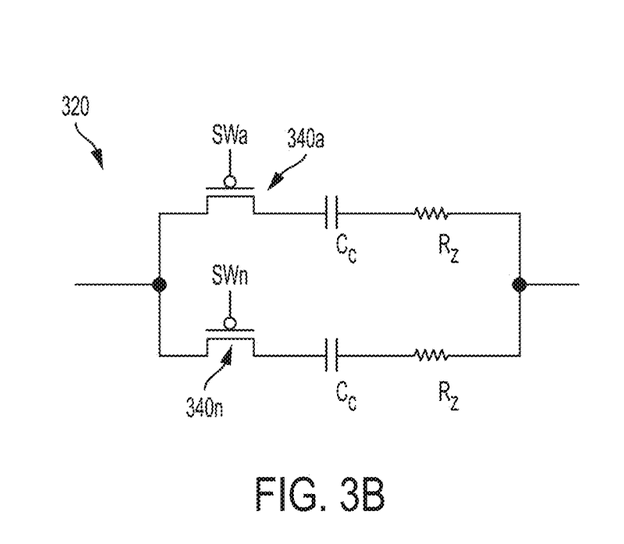
FIG. 3B is a circuit diagram of an implementation of one variable impedance circuit of FIG. 3A, according to a non-limiting embodiment of the present application.

FIG. 3B is a circuit diagram of an implementation of the variable impedance circuit 320 of FIG. 3A, according to a non-limiting embodiment of the present application. The variable impedance circuit 320 includes a number of switches 340a . . . 340n configured in parallel and configured to receive respective control signals SWa . . . SWn. In some embodiments, the digital controller 330 may provide the control signals SWa . . . SWn, although alternatives may be used. Each switch is coupled in series with a respective capacitor $C_c$ and resistor $R_Z$. The impedance of the variable impedance circuit 320 may be adjusted during an acquisition period through suitable provision of the control signals SWa . . . SWn. Any suitable number of parallel signal paths may be provided, so that the illustrated example of two parallel signal paths is non-limiting. The number of parallel signal paths and the capacitance and resistive values provided may be selected to provide sufficient control of the feedback impedance to account for the variable operation of the amplifier across the range of operating scenarios resulting from the variation of the variable current sources. For example, for a given amplifier gain dictated by variable feedback impedance 332, appropriate settings of variable impedance circuit 320 may be selected. In some embodiments, a lookup table may be utilized to determine the appropriate settings of variable impedance circuit 320 based on a given gain set by variable feedback impedance 332.

In both FIGS. 3A and 3B, the values of CC and RZ may be selected to provide desired operating characteristics. As examples, $R_z$ may be equal to 3 kOhms in some embodiments, and $C_C$ may be equal to 300 fF. Alternatives for both are possible. For example, they may assume values within +/−20% of those values listed, or any value or range of values within such ranges.

Figure 3C:
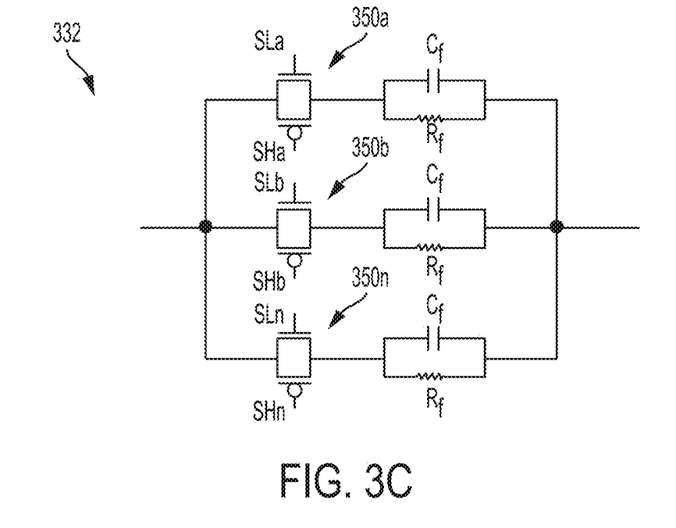
FIG. 3C is a circuit diagram of an implementation of another variable impedance circuit of FIG. 3A, according to a non-limiting embodiment of the present application

FIG. 3C is a circuit diagram of an implementation of the variable impedance circuit 332 of FIG. 3A, according to a non-limiting embodiment of the present application. The variable impedance circuit 332 includes a number of complementary switches 350a, 350b . . . 350n. Each switch receives respective control signals SLa, SLb . . . SLn and SHa, SHb . . . SHn. The control signals may be provided by the digital controller 330 in some embodiments, although alternatives may be used. The complementary switches are coupled to respective parallel-connected RC circuits $C_f$, $R_f$. While three complementary switches are shown in FIG. 3C, any suitable number may be provided to allow for sufficient control of the gain of the amplifier 300.

In both FIGS. 3A and 3C, the values of $C_f$ and $R_f$ may be selected to provide desired operating characteristics. As examples, $R_f$ may be equal to 180 kOhms in some embodiments, and $C_f$ may be equal to 84 fF. Alternatives for both are possible. For example, they may assume values within +/−20% of those values listed, or any value or range of values within such ranges.

Figure 4:
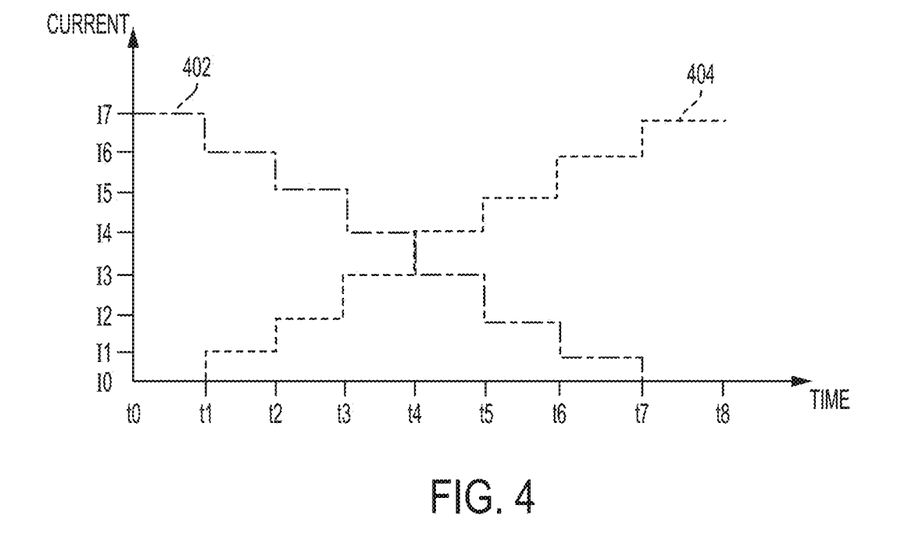
FIG. 4 is a graph illustrating the behavior of two variable current sources of an amplifier during an acquisition period, as may be implemented by the amplifier of FIGS. 2 and 3A, according to a non-limiting embodiment of the present application.

FIG. 4 is a graph illustrating the behavior of two variable current sources of a variable current amplifier during an acquisition period, as may be implemented by the amplifier of FIGS. 2 and 3A, which again may be a TIA. For example, the illustrated behavior may be implemented by the variable current sources 203 and 205 of FIG. 2. The x-axis represents time during an acquisition period, ranging from t0 to t8. The y-axis represents the current of the current source, having values ranging from I0 to I8. The values of t0-t8 and I0-I8 may be any suitable values for operation of a given ultrasound system, as the various aspects described herein are not limited to implementation of any specific time or current values. Also, the number of time intervals during an acquisition period is non-limiting, as more or fewer may be implemented. The number of current values which may be implemented is non-limiting, as more or fewer may be implemented.

Curve 402 represents the current of a variable current source of a second stage of a variable current amplifier. Thus, curve 402 may represent the current of current source 205 of FIG. 2. Curve 404 represents the current of a variable current source of a first stage of the variable current amplifier. Thus, curve 404 may represent the current of current source 203 of FIG. 2.

FIG. 4 illustrates that the currents of the first and second stages of the variable current amplifier move in opposing directions during the acquisition period. That is, curve 402 decreases moving from time t0 to time t8, while curve 404 increases during the same time. As previously described in connection with FIG. 2, the first and second stages of the variable current amplifier may impact different characteristics of the variable current amplifier behavior, such as noise and linearity. Thus, when operating in the manner illustrated in FIG. 4, the impact of the two stages of the variable current amplifier may vary during the acquisition period. That is, the impact of the second stage may be greater initially, up to time t4, while the impact of the first stage may be greater thereafter, from time t4 to time t8.

As previously described in connection with FIG. 3A, the currents of the two stages of a two-stage op-amp being used to implement a variable current amplifier may be controlled by digital codes. Thus, the current values I0-I7 of FIG. 4 may correspond to different digital codes set by a digital controller, such as digital controller 330 of FIG. 3A.

While FIG. 4 illustrates that the currents in the first and second stages of the amplifier switch at the same times, not all embodiments are limited in this respect. For example, the current in the second stage could be adjusted at times offset from those at which the current in the first stage is adjusted. Likewise, the currents of the two stages need not be adjusted the same number of times during an acquisition period.

Figure 5:
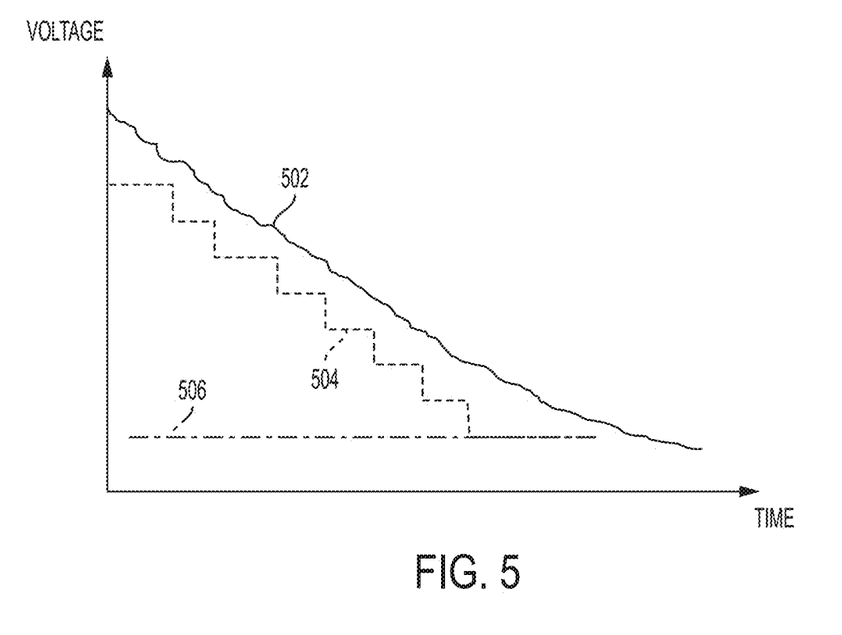
FIG. 5 is a graph illustrating an electrical signal representing an ultrasound signal, and a noise floor of an amplifier during an acquisition period, according to a non-limiting embodiment of the present application.

As described previously, an aspect of the present application provides an amplifier with a variable current source which is controlled to adjust the noise of the amplifier during an acquisition period. FIG. 5 illustrates an example of such operation.

In FIG. 5, the voltage of an electrical signal 502 output by an ultrasonic transducer, and thus representing a detected ultrasound signal, is illustrated as a function of time. Dashed line 504 represents the noise floor of an amplifier used to amplify the electrical signal 502, and may correspond to the noise floor of an amplifier of the types described herein, such as amplifier 112a. It can be seen that during the acquisition period, the magnitude of the electrical signal decreases. Likewise, the noise floor of the amplifier is decreased. Such a decrease in the noise floor may be achieved by controlling the current sunk by a variable current source of the amplifier in the manner described previously herein. For example, referring to FIG. 2, the variable current source 203 may be increased during the acquisition period to decrease the noise floor of the amplifier 112a. The noise floor may be adjusted to a level which provides an acceptable signal-to-noise ratio (SNR).

FIG. 5 also illustrates a constant noise floor 506. It can be seen that while the constant noise floor 506 is at the same level as dashed line 504 toward the end of the acquisition period, the constant noise floor 506 is lower than the value of the dashed line 504 up to that point. As has been described herein, the noise level of an amplifier may be dependent on the current consumed by the amplifier, and in such situations it should be appreciated that operating with a constant noise floor 506 requires significantly more current (and therefore power) than operating according to dashed line 504. Thus, aspects of the present application providing for a variable current amplifier to amplify ultrasound signals may provide substantial power savings compared to amplifiers operating with a constant noise level.

The amount of power savings may be significant. For example, in the circuit 100, the amplifiers 112a . . . 112n may consume a significant amount of power. In some embodiments, the amplifiers 112a . . . 112n may consume more power than any other components of the circuit 100. Accordingly, reducing the power consumption of the amplifiers 112a . . . 112n may provide a significant reduction in power of the circuit 100. In some embodiments, utilizing variable current amplifiers of the types described herein may provide up to a 25% power reduction, up to a 40% power reduction, up to a 50% power reduction, or any range or value within such ranges, in terms of the operation of the amplifier. The resulting power reduction for the circuit 100 may be up to 10%, up to 20%, up to 25%, or any range or value within such ranges.

Having thus described several aspects and embodiments of the technology of this application, it is to be appreciated that various alterations, modifications, and improvements will readily occur to those of ordinary skill in the art. Such alterations, modifications, and improvements are intended to be within the spirit and scope of the technology described in the application. It is, therefore, to be understood that the foregoing embodiments are presented by way of example only and that, within the scope of the appended claims and equivalents thereto, inventive embodiments may be practiced otherwise than as specifically described.

As an example, certain embodiments described herein have focused on two-stage amplifiers. However, the techniques described herein may apply to multi-stage amplifiers having two or more stages. When more than two stages are used, the first stage may predominantly control the noise of the amplifier, while the last stage may predominantly control the linearity of the amplifier.

As described, some aspects may be embodied as one or more methods. The acts performed as part of the method(s) may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The phrase "and/or," as used herein in the specification and in the claims, should be understood to mean "either or both" of the elements so conjoined, i.e., elements that are conjunctively present in some cases and disjunctively present in other cases.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements.

As used herein, the term "between" used in a numerical context is to be inclusive unless indicated otherwise. For example, "between A and B" includes A and B unless indicated otherwise.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

What is claimed is:

1. An ultrasound apparatus, comprising:
an ultrasound sensor;
a variable current trans-impedance amplifier (TIA) coupled to the ultrasound sensor and configured to receive and amplify an output signal from the ultrasound sensor, the variable current TIA being a multi-stage operational amplifier having a first stage and a last stage;
wherein the variable current TIA further comprises a variable impedance circuit coupled between an output terminal of the variable current TIA and a node representing an input to the last stage; and wherein the variable current TIA further comprises a variable feedback impedance circuit coupled between the output terminal of the variable current TIA and a node representing an input to the first stage.

2. The ultrasound apparatus of claim 1, wherein the variable current TIA includes a first variable current source coupled to the first stage and a second variable current source coupled to the last stage.

3. The ultrasound apparatus of claim 2, wherein the first and second variable current sources are independently controllable.

4. The ultrasound apparatus of claim 2, wherein the first and second variable current sources are digitally programmable.

5. The ultrasound apparatus of claim 2, further comprising a control circuit coupled to the first variable current source and the second variable current source and configured to control a first amount of current through the first variable current source and a second amount of current through the second variable current source.

6. The ultrasound apparatus of claim 5, wherein the control circuit is configured, when controlling the first amount of current through the first variable current source and the second amount of current through the second variable current source, to increase the first amount of current through the first variable current source in intervals during an acquisition period and to decrease the second amount of current through the second variable current source in intervals during the acquisition period.

7. The ultrasound apparatus of claim 5, wherein the control circuit is configured, when controlling the first amount of current through the first variable current source and the second amount of current through the second variable current source, to simultaneously increase the first amount of current through the first variable current source and decrease the second amount of current through the second variable current source after a time interval.

8. The ultrasound apparatus of claim 2, wherein the first variable current source provides eight states for a current of the first variable current source.

9. The ultrasound apparatus of claim 2, wherein the first variable current source comprises a first current source providing a first current, a second current source providing a second current, and a third current source providing a third current, the first current being approximately half of the second current and approximately a quarter of the third current.

10. The ultrasound apparatus of claim 1, wherein the ultrasound sensor and the variable current TIA are monolithically integrated on a semiconductor chip.

11. The ultrasound apparatus of claim 1, wherein the variable current TIA is configured, when amplifying the output signal, to decrease a noise floor of the variable current TIA during an acquisition period.

12. The ultrasound apparatus of claim 1, wherein the first variable impedance circuit comprises a first series of circuit components connected in parallel to a second series of circuit components, wherein:
the first series of circuit components comprises:
a first switch, a first capacitor, and a first resistor connected in series; or
a first switch connected in series with a parallel connection of a first capacitor and a first resistor; and
the second series of circuit components comprises:
a second switch, a second capacitor, and a second resistor connected in series; or
a second switch connected in series with a parallel connection of a second capacitor and a second resistor.

13. The ultrasound apparatus of claim 1, further comprising a control circuit configured to vary a feedback impedance of the variable impedance circuit based on a gain setting of the variable current TIA.

14. The ultrasound apparatus of claim 13, wherein the control circuit is further configured to vary a current of the variable current TIA in concert with varying the feedback impedance of the variable impedance circuit.

15. A method, comprising:
acquiring an ultrasound signal with an ultrasound sensor during an acquisition period and outputting, from the ultrasound sensor, an analog electrical signal representing the ultrasound signal; and
amplifying the analog electrical signal with a variable current trans-impedance amplifier (TIA) having a first stage, a last stage, a variable impedance circuit coupled between an output terminal of the variable current TIA and a node representing an input to the last stage, and a variable feedback impedance circuit coupled between the output terminal of the variable current TIA and a node representing an input to the first stage, wherein amplifying the analog electrical signal comprises varying a feedback impedance of the variable impedance circuit during the acquisition period.

16. The method of claim 15, wherein amplifying the analog electrical signal with the variable current TIA further comprises varying a current of the variable current TIA during the acquisition period.

17. The method of claim 16, wherein varying the feedback impedance of the variable impedance circuit further comprises varying the feedback impedance in concert with varying the current.

18. The method of claim 15, wherein varying the feedback impedance of the first variable impedance circuit during the acquisition period comprises varying the feedback impedance of the variable impedance circuit based on a gain setting of the variable current TIA.

19. The method of claim 15, wherein the variable impedance circuit comprises a first series of circuit components connected in parallel to a second series of circuit components, wherein:
the first series of circuit components comprises:
a first switch, a first capacitor, and a first resistor connected in series; or
a first switch connected in series with a parallel connection of a first capacitor and a first resistor; and
the second series of circuit components comprises:
a second switch, a second capacitor, and a second resistor connected in series; or
a second switch connected in series with a parallel connection of a second capacitor and a second resistor.

20. An ultrasound apparatus, comprising:
an ultrasound sensor; and
a variable current trans-impedance amplifier (TIA) coupled to the ultrasound sensor and configured to receive and amplify an output signal from the ultrasound sensor, the variable current TIA being a multi-stage operational amplifier having:
a first stage;
a last stage;
a first variable current source coupled to the first stage; and a second variable current source coupled to the last stage; and a control circuit coupled to the first variable current source and the second variable current source and configured to simultaneously increase a first amount of current through the first variable current source and decrease a second amount of current through the second variable current source after a time interval.

\* \* \* \* \*